United States Patent
Wachtler et al.

(10) Patent No.: US 9,119,395 B2
(45) Date of Patent: Sep. 1, 2015

(54) ACTIVE SUBSTANCE MIXTURES COMPRISING OPP AND AMINES, MICROBICIDAL AGENTS

(75) Inventors: Peter Wachtler, Krefeld (DE); Martin Kugler, Leichlingen (DE)

(73) Assignee: LANXESS Deutschland GmbH, Cologne (DE)

( * ) Notice: Subject to any disclaimer, the term of this patent is extended or adjusted under 35 U.S.C. 154(b) by 1134 days.

(21) Appl. No.: 12/090,030

(22) PCT Filed: Oct. 6, 2006

(86) PCT No.: PCT/EP2006/009678
§ 371 (c)(1),
(2), (4) Date: Apr. 11, 2008

(87) PCT Pub. No.: WO2007/042214
PCT Pub. Date: Apr. 19, 2007

(65) Prior Publication Data
US 2008/0234387 A1 Sep. 25, 2008

(30) Foreign Application Priority Data
Oct. 13, 2005 (DE) .......................... 10 2005 048 955

(51) Int. Cl.
*A01N 33/02* (2006.01)
*A01P 1/00* (2006.01)
*A01N 31/08* (2006.01)

(52) U.S. Cl.
CPC ..................................... *A01N 31/08* (2013.01)

(58) Field of Classification Search
USPC ........................................................ 514/673
See application file for complete search history.

(56) References Cited

U.S. PATENT DOCUMENTS

| 7,262,222 | B2 | 8/2007 | Carlson et al. |
| 7,481,973 | B2 | 1/2009 | Beilfuss et al. |
| 2002/0060823 | A1 | 5/2002 | Tomioka |
| 2002/0090349 | A1 | 7/2002 | Bergeron et al. |
| 2003/0012685 | A1 | 1/2003 | Wachtler et al. |
| 2003/0228373 | A1* | 12/2003 | Ludensky et al. ............. 424/600 |
| 2010/0093815 | A1 | 4/2010 | Wachtler et al. |

FOREIGN PATENT DOCUMENTS

| DE | 1928192 | 12/1970 |
| GB | 2354771 A | 4/2001 |
| WO | 9706675 A1 | 8/1996 |

OTHER PUBLICATIONS

International Search Report from co-pending Application PCT/EP2006/009678 dated Oct. 6, 2006, 18 pages.
F. C. Kull et al., "Mixtures of Quaternary Ammonium Compounds and Long-chain Fatty Acids as Antifungal Agents", Research Department, CIBA Pharmaceutical Products Inc., Summit New Jersey, Apr. 17, 1961, pp. 538-541.

* cited by examiner

*Primary Examiner* — Kathrien Cruz

(57) ABSTRACT

The invention relates to novel biocidal active substance mixtures containing o-phenylphenol and amines, methods for the production thereof, the use thereof for protecting technical materials and products from being infested and destroyed by microorganisms, and microbicidal agents based on said novel mixtures.

9 Claims, No Drawings

ACTIVE SUBSTANCE MIXTURES COMPRISING OPP AND AMINES, MICROBICIDAL AGENTS

CROSS REFERENCE TO RELATED PATENT APPLICATIONS

The present patent application claims the right of priority under 35 U.S.C. §119 (a)-(d) and 35 U.S.C. §365 of International Application No. PCT/EP2006/009678, filed 6 Oct. 2006, which was published in German as International Patent Publication No. WO 2007/042214 A1 on 19 Apr. 2007, which is entitled to the right of priority of German Patent Application No. DE 10 2005 0418 955.9 filed on 13 Oct. 2005.

The present application provides novel biocidal active compound mixtures comprising o-phenyphenol and amines, processes for their preparation and their use for protecting industrial materials and products against attack and destruction by microorganisms, and also microbicidal compositions based on these novel mixtures.

o-Phenylphenol (OPP) and its sodium and potassium salts are active compounds which have been used in practice for a long time for preparing microbicidally active preparations and disinfectants. In principle, these active compounds have broad antimicrobial action against microorganisms such as bacteria, fungi or yeasts and are distinguished in an advantageous manner by good chemical and thermal stability. However, owing to the relatively high lipophilicity of OPP, in some applications the efficacy is not always satisfactory, and as a consequence, the application concentrations required may be in a range which is unfavorable from a technical and economical point of view.

In the past, there has been no lack of efforts to improve the antimicrobial activity of OPP by combination with other active compounds.

Thus, for example, EP-A 150 250 06 describes a process in which the activity of OPP is to be improved by adding MIT.

WO 03/061641 describes a method which is based on the addition of further active compounds such as glutaraldehyde, adamantane or dodecylguanidine hydrochloride.

In some of the cases described above, an improvement of the microbiological activity is observed; however, in most cases the incorporation of the active compound components into the products to be protected requires an increased expense, since direct mixing of the particularly advantageously used OPP salts with most other biocides is, owing to chemical incompatibility, not easily possible, and the respective active compound components have to be added separately, which incurs apparative and logistical expenses.

Surprisingly, we have now found novel mixtures based on o-phenylphenol (OPP) and certain amines which, firstly, can be formulated in an advantageous manner and which, additionally, have an unexpected synergistic action when incorporated into industrial products which are microbiologically susceptible owing to their water content.

The present invention provides mixtures comprising o-phenylphenol and/or its sodium or potassium salt and at least one amine of the general formula (I)

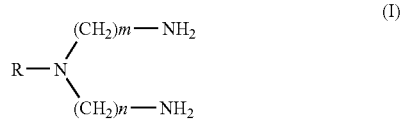

in which
R represents straight-chain or branched alkyl having 8 to 16 carbon atoms,
m and n each represent an integer of from 1 to 11,
with the proviso that the sum of n and m is from 4 to 12.

Preference is given to mixtures comprising at least one amine of the formula (I) in which
R represents straight-chain or branched alkyl having 10 to 14 carbon atoms,
m and n each represent an integer of from 1 to 7,
with the proviso that the sum of n and m is from 4 to 8.

Particular preference is given to mixtures comprising at least one amine of the formula (I) in which
R represents straight-chain or branched alkyl having 11 to 12 carbon atoms,
m and n each represent an integer of from 1 to 5,
with the proviso that the sum of n and m is from 4 to 6.

Very particular preference is given to mixtures comprising an amine of the general formula (I) in which R is dodecyl and n and m are 3.

The mixtures according to the invention are highly active against microorganisms and can be used for protecting industrial materials against attack and destruction by microorganisms.

In addition, the mixtures according to the invention are, surprisingly, distinguished in that, in specific mixing ratios, they have an unexpectedly high synergistic enhancement of activity. As a consequence, the application concentrations required for protecting industrial products may, in the case of the mixtures according to the invention, be reduced compared to the concentrations required in the case of the respective individual active compounds. This is extremely advantageous from an economical, ecological and technical point of view and contributes to increasing the preservation quality.

The mixtures according to the invention comprise OPP and an amine of the formula (I), preferably in synergistically effective amounts.

The amounts of o-phenylphenol and/or its sodium or potassium salt and an amine of the general formula (I) in the mixtures according to the invention can be varied within a relatively wide range. In general, the weight ratio of o-phenylphenol and/or its sodium or potassium salt to the amine of the general formula (I) is from 99:1 to 1:99, preferably from 50:1 to 1:50, particularly preferably from 10:1 to 1:10.

A further aspect of the invention relates to the fact that, if required, the components of the mixtures according to the invention can also be used as ready-mixed preparations, which distinguishes these mixtures advantageously from many other combination products comprising o-phenylphenol and/or its sodium or potassium salt and a second biocidal component.

The active compound mixtures according to the invention are preferably suitable for preserving functional fluids and water-containing industrial products susceptible to attack by microorganisms.

Applications for the following industrial materials and products may be mentioned by way of example, but not by way of limitation:
  chemical products for the building industry, such as concrete additives based, for example, on molasses, lignosulfonates or polyacrylates; bitumen emulsions or sealants
  printing thickeners based on natural products such as alginates, guar meals, gum arabic, corn, wheat or rice starches
  auxiliaries for the leather, textile or photochemical industry cooling lubricant concentrates and/or aqueous emulsions or dilutions thereof for metal processing based on mineral oil-containing, semi-synthetic or synthetic concentrates glues and adhesives based on raw materials of animal, vegetable or synthetic origin starch solutions or slurries slurries of other raw materials, such as color pigments (for example iron oxide pigments, carbon black pigments, titanium dioxide pigments) or slurries of fillers and coating pigments, such as kaolin, calcium carbonate, titanium dioxide or talc solvent-borne or water-borne inks Wax and clay emulsions The mixtures according to the invention may additionally comprise one or more other biocidally active compounds, or, when the mixtures according to the invention are employed, one or more of the biocidally active compounds mentioned below may be added separately. The compounds 1,2-benzisothiazol-3(2H)-one
1,2-dibromo-2,4-dicyanobutane (Tektamer 38)
2,2-diboromo-3-nitrlopropionamide (DBNPA)
2-bromo-2-nitropropane-1,3-diol (Bronopol)
5-chloro-2-methyl-4-isothazolin-3-one/2-methyl-4-isothazolin-3-one (CMIT/MIT)
benzyl alcohol
bromochlorodimethylhydantoin
diazolidinylurea
dichlorobenzyl alcohol
didecycldimethyl ammonium chloride
3,3-dimethylol-5,5-dimethylhydantoin
ethylene glycol hemiformal
ethylene glycol bishemiformal
imidazolindinylurea
2-methyl-4-isothlazolin-3-one
phenoxyethanol
phenylethyl alcohol
poly(hexamethylenebiguanide) hydrochloride
tetramethylolacetylenediurea (TMAD)
tetrakis(hydroxymethyl)phosphonium sulfate (THPS)

may be mentioned as preferred co-components.

In the protection of materials, the mixtures according to the invention are used for protecting industrial materials, in particular for protecting aqueous functional fluids and water-containing industrial products.

They are effective against microorganisms of the most different types, such as, for example, bacteria, molds, yeasts and also slime organisms.

The following species may be mentioned by way of example, but not by way of limitation.

Bacteria:
*Alcaligenes*, such as *Alcaligenes faecalis*, *Bacillus*, such as *Bacillus subtilis*, *Escherichia*, such as *Escherichia coli*, *Proteus*, such as *Proteus vulgaris*, *Pseudomonas*, such as *Pseudomonas aeruginosa* or *Pseudomonas fluorescens*, *Staphylococcus*, such as *Staphylococcus aureus*.

Yeasts:
*Candida*, such as *Candida albicans*, *Geotrichum*, such as *Geotrichum candidum*, *Rhodotorula*, such as *Rhodotorula rubra*, *Saccharomyces*, such as *Saccharomyces cerevisiae*.

Fungi:
*Alternaria*, such as *Alternaria tenuis*, *Aspergillus*, such as *Aspergillus niger*, *Chaetomium*, such as *Chaetomium globosum*, *Fusarium*, such as *Fusarium solani*, *Lentinus*, such as *Lentinus tigrinus*, *Paecilomyces*, such as *Paecilomyces variotti*, *Penicillitim*, such as *Penicillium glaucum*.

The mixtures according to the invention can be prepared by mixing the individual components with one another, if appropriate with addition of one or more solvents and, if appropriate, further antimicrobially active compounds.

Depending on their respective physical and/or chemical properties, the mixtures according to the invention can be applied either separately in the form of a metered addition of the individual active compounds, in which case the concentration ratio may be individually adjusted depending on the preservation problem present, or a finished active compound mixture may be metered in. For this, it is possible to convert the mixture according to the invention beforehand into a customary formulation, such as, for example, a solution, emulsion, suspension powder, foam, pastes, granules, aerosols and microencapsulations in polymeric substances.

These formulations may be prepared in a manner known per se, for example by mixing the mixture according to the invention or the individual active compounds comprised therein with extenders, i.e. liquid solvents, pressurized liquefied gases and/or solid carriers, if appropriate with the use of surfactants, i.e. emulsifiers and/or dispersants and/or foam formers. If the extender used is water, it is also possible to use, for example, organic solvents as auxiliary solvents. Essentially, suitable liquid solvents include: alcohols, such as butanol or glycol, and also ethers and esters thereof, ketones, such as acetone, methyl ethyl ketone, methyl isobutyl ketone or cyclohexanone, strongly polar solvents, such as dimethylformamide, N-methylpyrrolidone or dimethyl sulfoxide, and also water; liquefied gaseous extenders or carriers are to be understood as meaning liquids which are gaseous at ambient temperature and under atmospheric pressure, for example aerosol propellants, such as halogenated hydrocarbons, and also butane, propane, nitrogen and carbon dioxide; suitable solid carriers are: for example ground natural minerals, such as kaolins, clays, talc, chalk, quartz, attapulgite, montmorillonite or diatomaceous earth, and ground synthetic minerals, such as finely divided silica, aluminum oxide and silicates; suitable solid carriers for granules are: for example crushed and fractionated natural rocks, such as calcite, marble, pumice, sepiolite and dolomite, and also synthetic granules of inorganic and organic meals, and granules of organic materials such as sawdust, coconut shells, corn cobs and tobacco stalks; suitable emulsifiers and/or foam formers are: for example nonionic and anionic emulsifiers, such as polyoxyethylene fatty acid esters, polyoxyethylene fatty alcohol ethers, for example alkylaryl polyglycol ethers, alkylsulfonates, alkyl sulfates, arylsulfonates, and also protein hydrolysates; suitable dispersants are: for example lignosulfite waste liquors or polyacrylates.

Tackifiers and thickeners such as carboxymethylcellulose, methylcellulose and natural and synthetic polymers in the form of powders, granules or latices, such as gum arabic, polyvinyl alcohol, polyvinyl acetate, and also natural phospholipids, such as cephalins and lecithins and synthetic phospholipids can be used in the formulations. Other possible additives are mineral and vegetable oils.

The present invention furthermore provides microbicidal compositions based on the mixtures according to the invention, which compositions comprise at least one solvent or diluent and also, if appropriate, processing auxiliaries and, if appropriate, further antimicrobially active substances.

The microbicidal compositions or formulated concentrates used for protecting industrial materials comprise the active compounds o-phenylphenol and/or its sodium or potassium salt and an amine of the general formula (I), calculated as the sum of the two active compounds, in a concentration of from 5 to 80% by weight, preferably from 10 to 60% by weight.

The application concentrations of the active compound combinations to be used according to the invention depend on the nature and the occurrence of the microorganisms to be controlled, on the initial microbial load, on the expected storage time of the products to be protected and on the composition of the end products at risk from microbiological attack. The optimum amount to be employed can be determined by preliminary tests and test series on a laboratory scale and by supplementary operational tests. In general, the use concentrations are in the range of from 0.01 to 5% by weight, preferably from 0.02 to 2.0% by weight, of the mixture according to the invention, based on the material to be protected.

The surprising high efficacy of the mixtures according to the invention is documented in the examples below:

EXAMPLES

There are certain germs which are particularly relevant in practice, such as, for example, *Pseudnomonas fluorescens* (Example 1), where the mixtures according to the invention are notable for synergistic effects, i.e. the activity of the mixture is greater than the activity of the individual components would have suggested.

The observed synergism of the mixtures according to the invention can be determined by the following mathematical approach (cf. F. C. Kull, P. C. Elisman, H. D. Sylwestrowicz and P. K. Mayer, Appl. Microbiol, 9, 538 (1961):

$$\text{synergistic index } (SI) = \frac{Q_a}{Q_A} + \frac{Q_b}{Q_B}$$

where $Q_a$=the amount of component A in the active compound mixture required to achieve the desired effect, i.e. no microbial growth, $Q_A$=the amount of component A which, applied on its own, suppresses the growth of the microorganisms, $Q_b$=the amount of component B in the active compound mixture which suppresses the growth of the microorganisms, $Q_b$=the amount of component B which, applied on its own, suppresses the growth of the microorganisms.

A synergistic index of SI<1, in accordance with the above formula, indicates a synergistic effect for the active compound mixture.

Using the calculations below, the synergistic enhancement of activity is illustrated by way of example, but not by way of limitation.

Example 1

Synergism o-phenylphenol (OPP)/bis(3-aminopropyl)dodecylamine "AMINE 1")

The minimum inhibitory concentration of the active compound combinations listed in Table 1 were examined using the test germ *Pseudomonas fluorescens*

TABLE 1

*Pseudomonas fluorescens*

|  |  | SI |
|---|---|---|
|  | Amount of pure active compounds required to suppress growth (in ppm) |  |
| A = OPP | 500 (=$Q_A$) |  |
| B = "AMINE 1" | 50 (=$Q_B$) |  |
|  | Proportional amounts in the active compound mixtures required to suppress growth (in ppm) |  |
| OPP/"AMINE 1" (9:1)* | ($Q_a$) = 90/($Q_b$) = 10 | 0.38 |
| OPP/"AMINE 1" (8:2)* | ($Q_a$) = 80/($Q_b$) = 20 | 0.66 |
| OPP/"AMINE 1" (7:3)* | ($Q_a$) = 70/($Q_b$) = 30 | 0.74 |
| OPP/"AMINE 1" (6:4)* | ($Q_a$) = 30/($Q_b$) = 20 | 0.46 |
| OPP/"AMINE 1" (5:5)* | ($Q_a$) = 25/($Q_b$) = 25 | 0.55 |
| OPP/"AMINE 1" (4:6)* | ($Q_a$) = 20/($Q_b$) = 30 | 0.64 |
| OPP/"AMINE 1" (3:7)* | ($Q_a$) = 15/($Q_b$) = 35 | 0.71 |
| OPP/"AMINE 1" (2:8)* | ($Q_a$) = 10/($Q_b$) = 40 | 0.80 |
| OPP/"AMINE 1" (1:9)* | ($Q_a$) = 90/($Q_b$) = 10 | 0.90 |

*(in brackets = weight ratios of the active compounds in the mixture)

The combinations according to the invention have a pronounced synergistic activity.

Example 2

Preservation of a Chalk Suspension

The preserving action of an active compound mixture according to the invention was examined in a chalk suspension using a preservation stress test.
Microbiological Stress Test The microbiological stress test examines the susceptibility of water-based systems to microbial attack and the action of preservatives. To this end, the preservatives are incorporated in defined concentrations into the water-based systems. To simulate praxis-like conditions, depending on the medium to be examined, a storage at elevated temperatures (for example 7 days at 40° C., 3 days at 60° C. or the like) may be carried out prior to the actual preservation test to evaluate the preservatives to be examined under conditions which are as realistic as possible. After the preparations have been carried out, contamination with microorganisms of a defined species is carried out at weekly intervals over a test period of at most 6 weeks. 2-3 and 7 days after each contamination, by counting the number of germs, it is established whether a complete kill or at least inhibition of propagation of the bacteria introduced has been achieved, compared to the unpreserved control samples.

The contamination source used for the examination in the stress test was the following microorganism mixture:
*Pseudomonas aeruginosa*
*Pseudomonas fluorescens*
*Pseudomonas oleovorans*
*Pseudomonas rubescens*
*Pseudomonas stutzeri*
*Alcalaigenes faecalis*
*Citrobacter freundii*
*Corynebacterium* sp.

Very good activity is achieved when, even after 6 contamination cycles, the reserved samples effect a kill of the microorganisms introduced. Satisfactory activity is present if, compared to the unpreserved sample, a strongly reduced level of microbes is observed.

Results

Using a chalk suspension (proportion of solids 70-75%), a preservation stress test according to the above scheme was carried out. After incorporation of the respective biocidally active compounds at the stated concentrations, the samples were exposed to thermal stress at 60° C. for 3 days. The samples pre-treated in this manner were then used for carrying out the microbiological stress test.

TABLE

| Biocides Dosages | Week 1 | Week 2 | Week 3 | Week 4 | Week 5 | Week 6 |
|---|---|---|---|---|---|---|
| o-Phenylphenol (OPP) | | | | | | |
| 200 ppm | ok | ok | ok | ok | spoilt | spoilt |
| 150 ppm | ok | spoilt | spoilt | spoilt | spoilt | spoilt |
| Bis(3-aminopropyl)-dodecylamine ("Amine 1") | | | | | | |
| 80 ppm | ok | spoilt | spoilt | spoilt | spoilt | spoilt |
| 160 ppm | ok | ok | ok | spoilt | spoilt | spoilt |
| O Phenylphenol & "Amine 1" | | | | | | |
| OPP = 200 ppm & "Amine 1" = 80 ppm | ok | ok | ok | ok | ok | ok |

As can be seen from the above table, by adding the mixture according to the invention of o-phenylphenol and bis(3-aminopropyl)dodecylamine ("Amine 1"), it is possible to achieve an activity which is significantly improved compared to the individual compounds, resulting in a preservation action which is improved altogether in that the material to be protected remains in a germ-free state over the entire period of the 6-week test protocol with 6 consecutive inoculations.

The present invention is described with reference to specific details of particular embodiments thereof. It is not intended that such details be regarded as limitations upon the scope of the invention except insofar as and to the extent that they are included in the accompanying claims.

What is claimed is:

1. A mixture comprising o-phenylphenol and/or its sodium or potassium salt (N, N-bis(3-aminopropyl)dodecylamine, with a weight ratio of o-phenylphenol and/or it's sodium or potassium salt of (N, N-bis(3-aminopropyl)dodecylamine is from 1:9 to 9:1,
   wherein the mixture has a synergistic effect.

2. A microbicidal composition, comprising:
   the mixture according to claim 1; and
   at least one auxiliary from the group of solvents, solvent mixtures, extenders, and surfactants.

3. A process for protecting industrial materials against attack and/or destruction by microorganisms, comprising:
   contacting said with the mixture according to claim 1.

4. The process according to claim 3, wherein the industrial materials are water-containing industrial products or water-containing functional fluids.

5. A process for preparing the composition according to claim 2, comprising:
   mixing the o-phenylphenol with the at least one amine of the formula (I); and
   adding the at least one auxiliary.

6. The microbicidal composition according to claim 2, further comprising:
   a further antimicrobially active compound.

7. A process for protecting industrial materials against attack and/or destruction by microorganisms, comprising:
   contacting said industrial materials with the composition according to claim 2.

8. The process according to claim 7, wherein the industrial materials are water-containing industrial products or water-containing functional fluids.

9. A process for preparing the composition according to claim 6, comprising:
   mixing the o-phenylphenol with (N,N-bis(3-aminopropyl)dodecylamine;
   adding the at least one auxiliary; and
   adding the further antimicrobially active compound.

* * * * *